(12) United States Patent
Wenning et al.

(10) Patent No.: US 12,741,135 B2
(45) Date of Patent: Sep. 22, 2026

(54) SYSTEM AND METHOD FOR CONTROLLING A CARDIAC ASSISTANCE SYSTEM

(71) Applicant: Kardion GmbH, Stuttgart (DE)

(72) Inventors: Leon Wenning, Stuttgart (DE); Inga Schellenberg, Stuttgart (DE); Annika Bach, Leutenbach (DE)

(73) Assignee: KARDION GMBH, Stuttgart (DE)

( * ) Notice: Subject to any disclaimer, the term of this patent is extended or adjusted under 35 U.S.C. 154(b) by 665 days.

(21) Appl. No.: 17/290,083

(22) PCT Filed: Oct. 31, 2019

(86) PCT No.: PCT/EP2019/079905
§ 371 (c)(1),
(2) Date: Apr. 29, 2021

(87) PCT Pub. No.: WO2020/089429
PCT Pub. Date: May 7, 2020

(65) Prior Publication Data

US 2021/0393944 A1 Dec. 23, 2021

(30) Foreign Application Priority Data

Nov. 2, 2018 (DE) ..................... 10 2018 218 770.3

(51) Int. Cl.
*A61M 60/585* (2021.01)
*A61M 60/178* (2021.01)
(Continued)

(52) U.S. Cl.
CPC ........ *A61M 60/585* (2021.01); *A61M 60/178* (2021.01); *A61M 60/216* (2021.01);
(Continued)

(58) Field of Classification Search
CPC .............. A61M 60/585; A61M 60/178; A61M 60/216; A61M 60/508; A61M 60/592;
(Continued)

(56) References Cited

U.S. PATENT DOCUMENTS 2,254,698 A 9/1941 Hansen, Jr.
3,085,407 A 4/1963 Tomlinson
(Continued)

FOREIGN PATENT DOCUMENTS

CA 3 000 581 4/2017
CA 3 122 415 7/2020
(Continued)

OTHER PUBLICATIONS

Murali A; "Design of Inductive Coils for Wireless Power Transfer to Pediatric Implants, A graduate project submitted in partial fulfillment of the requirements For the degree of Master of Science in Electrical Engineering;" California State University, Northridge, May 2018 (Year: 2018).*
(Continued)

*Primary Examiner* — Jennifer Pitrak McDonald
*Assistant Examiner* — Christopher J. Mutchler
(74) *Attorney, Agent, or Firm* — Knobbe Martens Olson and Bear, LLP

(57) ABSTRACT

The invention relates to a system (100) and a method (500) for controlling a cardiac support system (10), comprising a first extracorporeal control device (110), wherein the first control device (110) is or can be connected to the cardiac support system (10) with a wire or a first coil (150) for communication and/or energy transfer, and comprising a second extracorporeal control device (120) which is wirelessly connected to the first control device (110). The invention also relates to a cardiac support system (10) having a control system according to the invention (100).

20 Claims, 2 Drawing Sheets

(51) Int. Cl.
*A61M 60/216* (2021.01)
*A61M 60/508* (2021.01)
*A61M 60/592* (2021.01)
*A61M 60/873* (2021.01)
*A61M 60/88* (2021.01)

(52) U.S. Cl.
CPC ........ *A61M 60/508* (2021.01); *A61M 60/592* (2021.01); *A61M 60/873* (2021.01); *A61M 60/88* (2021.01); *A61M 2205/18* (2013.01); *A61M 2205/505* (2013.01)

(58) Field of Classification Search
CPC ................ A61M 60/873; A61M 60/88; A61M 2205/18; A61M 2205/505; A61M 2205/17; H02J 2310/23; H02J 7/00034; H02J 50/80; H02J 50/10; G06F 3/038; G06F 2203/0382; H04W 4/00; H04W 4/80; G08B 21/0247
See application file for complete search history.

(56) References Cited

U.S. PATENT DOCUMENTS 3,088,323 A 5/1963 Welkowitz et al.
3,614,181 A 10/1971 Meeks
3,645,268 A 2/1972 Capote
3,747,998 A 7/1973 Klein et al.
3,790,878 A 2/1974 Brokaw
3,807,813 A 4/1974 Milligan
4,023,562 A 5/1977 Hynecek et al.
4,441,210 A 4/1984 Hochmair et al.
4,680,730 A 7/1987 Omoda
4,781,525 A 11/1988 Hubbard et al.
4,888,009 A 12/1989 Lederman et al.
4,888,011 A 12/1989 Kung et al.
4,896,754 A 1/1990 Carlson et al.
4,902,272 A 2/1990 Milder et al.
5,000,177 A 3/1991 Hoffmann et al.
5,195,877 A 3/1993 Kletschka
5,269,811 A 12/1993 Hayes
5,289,821 A 3/1994 Swartz
5,443,503 A 8/1995 Yamane
5,456,715 A 10/1995 Liotta
5,527,159 A 6/1996 Bozeman, Jr. et al.
5,581,038 A 12/1996 Lampropoulos
5,599,173 A 2/1997 Chen et al.
5,606,972 A 3/1997 Routh
5,613,935 A 3/1997 Jarvik
5,629,661 A 5/1997 Ooi et al.
5,662,115 A 9/1997 Torp
5,676,651 A 10/1997 Larson, Jr. et al.
5,690,674 A 11/1997 Diaz
5,702,430 A 12/1997 Larson, Jr. et al.
5,713,954 A 2/1998 Rosenberg et al.
5,720,771 A 2/1998 Snell
5,752,976 A 5/1998 Duffin et al.
5,766,207 A 6/1998 Potter et al.
5,814,900 A 9/1998 Esser
5,827,203 A 10/1998 Nita
5,843,141 A 12/1998 Bischoff et al.
5,865,759 A 2/1999 Koblanski
5,888,242 A 3/1999 Antaki et al.
5,911,685 A 6/1999 Siess et al.
5,964,694 A 10/1999 Siess et al.
5,982,153 A 11/1999 Nagal
6,007,478 A 12/1999 Siess et al.
6,053,873 A 4/2000 Govari et al.
6,058,958 A 5/2000 Benkowski et al.
6,149,405 A 11/2000 Abe et al.
6,167,765 B1 1/2001 Weitzel
6,176,822 B1 1/2001 Nix et al.
6,183,412 B1 2/2001 Benkowsi et al.
6,185,460 B1 2/2001 Thompson
6,210,318 B1 4/2001 Lederman
6,212,430 B1 4/2001 Kung et al.
6,224,540 B1 5/2001 Lederman et al.
6,231,498 B1 5/2001 Pfeiffer et al.
6,245,007 B1 6/2001 Bedingham et al.
6,254,359 B1 7/2001 Aber
6,264,601 B1 7/2001 Jassawalla et al.
6,324,430 B1 11/2001 Zarinetchi et al.
6,324,431 B1 11/2001 Zarinetchi et al.
6,351,048 B1 2/2002 Schob et al.
6,361,292 B1 3/2002 Chang et al.
6,366,817 B1 4/2002 Kung
6,389,318 B1 5/2002 Zarinetchi et al.
6,398,734 B1 6/2002 Cimochowski et al.
6,400,991 B1 6/2002 Kung
6,432,136 B1 8/2002 Weiss et al.
6,442,434 B1 8/2002 Zarinetchi et al.
6,445,956 B1 9/2002 Laird et al.
6,471,713 B1 10/2002 Vargas et al.
6,496,733 B2 12/2002 Zarinetchi et al.
6,508,756 B1 1/2003 Kung et al.
6,512,949 B1 1/2003 Combs et al.
6,516,227 B1 2/2003 Meadows et al.
6,527,698 B1 3/2003 Kung et al.
6,530,876 B1 3/2003 Spence
6,540,658 B1 4/2003 Fasciano et al.
6,540,659 B1 4/2003 Milbocker
6,553,263 B1 4/2003 Meadows et al.
6,561,975 B1 5/2003 Pool et al.
6,579,257 B1 6/2003 Elgas et al.
6,592,620 B1 7/2003 Lancisi et al.
6,602,182 B1 8/2003 Milbocker
6,605,032 B2 8/2003 Benkowsi et al.
6,652,447 B2 11/2003 Benkowsi et al.
6,731,976 B2 5/2004 Penn et al.
6,879,126 B2 4/2005 Paden et al.
6,912,423 B2 6/2005 Ley et al.
6,949,066 B2 9/2005 Bearnson et al.
6,979,338 B1 12/2005 Loshakove et al.
6,984,201 B2 1/2006 Khaghani et al.
7,010,954 B2 3/2006 Siess
7,022,100 B1 4/2006 Aboul-Hosn et al.
7,024,244 B2 4/2006 Muhlenberg et al.
7,062,331 B2 6/2006 Zarinetchi et al.
7,070,398 B2 7/2006 Olsen et al.
7,083,588 B1 8/2006 Shmulewitz et al.
7,138,776 B1 11/2006 Gauthier et al.
7,155,291 B2 12/2006 Zarinetchi et al.
7,160,243 B2 1/2007 Medvedev
7,175,588 B2 2/2007 Morello
7,177,681 B2 2/2007 Xhu
7,238,151 B2 7/2007 Frazier
7,338,521 B2 3/2008 Antaki et al.
7,396,327 B2 7/2008 Morello
7,513,864 B2 4/2009 Kantrowitz et al.
7,520,850 B2 4/2009 Brockway
7,526,338 B1 4/2009 Gill
7,527,599 B2 5/2009 Hickey
7,591,777 B2 9/2009 LaRose
7,762,941 B2 7/2010 Jarvik
7,794,384 B2 9/2010 Sugiura et al.
7,819,916 B2 10/2010 Yaegashi
7,850,593 B2 12/2010 Vincent et al.
7,850,594 B2 12/2010 Sutton et al.
7,856,335 B2 12/2010 Morello et al.
7,862,501 B2 1/2011 Woodward et al.
7,942,805 B2 5/2011 Shambaugh, Jr.
7,951,062 B2 5/2011 Morello
7,959,551 B2 6/2011 Jarvik
7,963,905 B2 6/2011 Salmonsen et al.
7,988,728 B2 8/2011 Ayre
8,012,079 B2 9/2011 Delgado, III
8,075,472 B2 12/2011 Zilbershlag et al.
8,088,059 B2 1/2012 Jarvik
8,190,390 B2 5/2012 Morello et al.
8,231,519 B2 7/2012 Reichenbach et al.
8,303,482 B2 11/2012 Schima et al.
8,323,173 B2 12/2012 Benkowsi et al.
8,435,182 B1 5/2013 Tamura
8,461,817 B2 6/2013 Martin et al.

(56) References Cited

U.S. PATENT DOCUMENTS 8,489,200 B2 7/2013 Zarinetchi et al.
8,545,380 B2 10/2013 Farnan et al.
8,585,572 B2 11/2013 Mehmanesh
8,591,393 B2 11/2013 Walters et al.
8,608,635 B2 12/2013 Yomtov et al.
8,612,002 B2 12/2013 Faltys et al.
8,620,447 B2 12/2013 D'Ambrosio et al.
8,622,949 B2 1/2014 Zafirelis et al.
8,657,733 B2 2/2014 Ayre et al.
8,657,875 B2 2/2014 Kung et al.
8,715,151 B2 5/2014 Poirier
8,747,293 B2 6/2014 Arndt et al.
8,766,788 B2 7/2014 D'Ambrosio
8,827,890 B2 9/2014 Lee et al.
8,849,398 B2 9/2014 Evans
8,862,232 B2 10/2014 Zarinetchi et al.
8,864,643 B2 10/2014 Reichenbach et al.
8,864,644 B2 10/2014 Yomtov
8,870,739 B2 10/2014 LaRose et al.
8,897,873 B2 11/2014 Schima et al.
8,900,114 B2 12/2014 Tansley et al.
8,961,389 B2 2/2015 Zilbershlag
9,002,468 B2 4/2015 Shea et al.
9,002,469 B2 4/2015 D'Ambrosio
9,071,182 B2 6/2015 Yoshida et al.
9,091,271 B2 7/2015 Bourque
9,220,826 B2 12/2015 D'Ambrosio
9,283,314 B2 3/2016 Prasad et al.
9,297,735 B2 3/2016 Graichen et al.
9,308,305 B2 4/2016 Chen et al.
9,364,592 B2 6/2016 McBride
9,371,826 B2 6/2016 Yanai et al.
9,381,286 B2 7/2016 Spence et al.
9,427,508 B2 8/2016 Reyes et al.
9,427,509 B2 8/2016 Vodermayer
9,440,013 B2 9/2016 Dowling et al.
9,456,898 B2 10/2016 Barnes et al.
9,474,840 B2 10/2016 Siess
9,486,566 B2 11/2016 Siess
9,492,600 B2 11/2016 Strueber et al.
9,492,601 B2 11/2016 Casas et al.
9,511,179 B2 12/2016 Casas et al.
9,539,094 B2 1/2017 Dale et al.
9,556,873 B2 1/2017 Yanai et al.
9,561,362 B2 2/2017 Malinowski
9,566,374 B2 2/2017 Spence et al.
9,569,985 B2 2/2017 Alkhatib et al.
9,592,397 B2 3/2017 Hansen et al.
9,603,984 B2 3/2017 Romero et al.
9,616,107 B2 4/2017 VanAntwerp et al.
9,636,442 B2 5/2017 Karmon et al.
9,656,010 B2 5/2017 Burke
9,669,142 B2 6/2017 Spanier et al.
9,669,144 B2 6/2017 Spanier et al.
9,694,123 B2 7/2017 Bourque et al.
9,713,701 B2 7/2017 Sarkar et al.
9,717,831 B2 8/2017 Schuermann
9,724,083 B2 8/2017 Quadri et al.
9,744,282 B2 8/2017 Rosenberg et al.
9,789,236 B2 10/2017 Bonde
9,800,172 B1 10/2017 Leabman
9,833,314 B2 12/2017 Corbett
9,833,550 B2 12/2017 Siess
9,833,611 B2 12/2017 Govea et al.
9,848,899 B2 12/2017 Sliwa et al.
9,849,224 B2 12/2017 Angwin et al.
9,878,087 B2 1/2018 Richardson et al.
9,943,236 B2 4/2018 Bennett et al.
9,950,102 B2 4/2018 Spence et al.
9,974,894 B2 5/2018 Morello
9,999,714 B2 6/2018 Spanier et al.
10,010,412 B2 7/2018 Taft
10,010,662 B2 7/2018 Wiesener et al.
10,022,480 B2 7/2018 Greatrex et al.
10,052,420 B2 8/2018 Medvedev et al.
10,143,571 B2 12/2018 Spence et al.
10,148,126 B2 12/2018 Hoarau
10,279,093 B2 5/2019 Reichenbach et al.
10,376,162 B2 8/2019 Edelman et al.
10,413,651 B2 9/2019 Yomtov et al.
10,426,879 B2 10/2019 Farnan
10,449,275 B2 10/2019 Corbett
10,463,508 B2 11/2019 Spence et al.
10,500,322 B2 12/2019 Karch
10,525,178 B2 1/2020 Zeng
10,549,020 B2 2/2020 Spence et al.
10,561,771 B2 2/2020 Heilman et al.
10,561,773 B2 2/2020 Ferrari et al.
10,632,241 B2 4/2020 Schenck et al.
10,668,195 B2 6/2020 Flores
10,732,583 B2 8/2020 Rudser
10,857,275 B2 12/2020 Granegger
10,864,308 B2 12/2020 Muller et al.
10,944,293 B2 3/2021 Nakao
11,000,282 B2 5/2021 Schuelke et al.
11,056,878 B2 7/2021 Gao et al.
11,065,437 B2 7/2021 Aber et al.
11,067,085 B2 7/2021 Granegger et al.
11,071,857 B2 7/2021 Sun
11,103,715 B2 8/2021 Fort
11,110,265 B2 9/2021 Johnson
11,120,908 B2 9/2021 Agnello et al.
11,121,580 B2 9/2021 Partovi
11,131,968 B2 9/2021 Rudser
11,154,701 B2 10/2021 Reyes et al.
11,154,702 B2 10/2021 Kadrolkar et al.
11,179,559 B2 11/2021 Hansen
11,185,682 B2 11/2021 Farnan
11,191,945 B2 12/2021 Siess et al.
11,197,618 B2 12/2021 Edelman et al.
11,217,344 B2 1/2022 Agnello
11,224,737 B2 1/2022 Petersen et al.
11,235,139 B2 2/2022 Kudlik
11,241,572 B2 2/2022 Dague et al.
11,266,502 B1 3/2022 Wallace
11,273,299 B2 3/2022 Wolman et al.
11,285,310 B2 3/2022 Curran et al.
11,285,311 B2 3/2022 Siess et al.
11,291,826 B2 4/2022 Tuval et al.
11,298,524 B2 4/2022 El Katerji et al.
11,311,711 B2 4/2022 Casas et al.
11,316,371 B1 4/2022 Partovi et al.
11,316,679 B2 4/2022 Agnello
11,317,988 B2 5/2022 Hansen et al.
11,337,724 B2 5/2022 Masubuchi et al.
11,338,125 B2 5/2022 Liu et al.
11,344,717 B2 5/2022 Kallenbach et al.
11,351,356 B2 6/2022 Mohl
11,351,357 B2 6/2022 Mohl
11,351,358 B2 6/2022 Nix et al.
11,351,359 B2 6/2022 Clifton et al.
11,351,360 B2 6/2022 Rudser et al.
11,357,438 B2 6/2022 Stewart et al.
11,357,968 B2 6/2022 El Katerji et al.
11,368,081 B2 6/2022 Vogt et al.
11,369,785 B2 6/2022 Callaway et al.
11,369,786 B2 6/2022 Menon et al.
11,376,415 B2 7/2022 Mohl
11,376,419 B2 7/2022 Reyes et al.
11,389,641 B2 7/2022 Nguyen et al.
11,406,483 B2 8/2022 Wirbisky et al.
11,406,520 B2 8/2022 Lam
11,406,802 B2 8/2022 DeGraaf et al.
11,413,443 B2 8/2022 Hodges et al.
11,413,444 B2 8/2022 Nix et al.
11,413,445 B2 8/2022 Brown et al.
11,420,041 B2 8/2022 Karch
11,439,806 B2 9/2022 Kimball et al.
11,446,481 B2 9/2022 Wolman et al.
11,471,692 B2 10/2022 Aghassian et al.
11,478,629 B2 10/2022 Harjes et al.
11,497,906 B2 11/2022 Grace et al.
11,517,737 B2 12/2022 Struthers et al.
11,517,738 B2 12/2022 Wisniewski

(56) References Cited

U.S. PATENT DOCUMENTS 11,517,740 B2 12/2022 Agarwa et al.
11,521,723 B2 12/2022 Liu et al.
11,524,165 B2 12/2022 Tan et al.
11,527,322 B2 12/2022 Agnello et al.
11,529,062 B2 12/2022 Moyer et al.
11,529,508 B2 12/2022 Jablonsk et al.
11,554,260 B2 1/2023 Reyes et al.
11,572,879 B2 2/2023 Mohl
11,574,741 B2 2/2023 Tan et al.
11,577,068 B2 2/2023 Spence et al.
11,581,083 B2 2/2023 El Katerji et al.
11,583,659 B2 2/2023 Pfeffer et al.
11,583,671 B2 2/2023 Nguyen et al.
11,587,337 B2 2/2023 Lemay et al.
11,590,337 B2 2/2023 Granegger et al.
11,596,727 B2 3/2023 Siess et al.
11,602,624 B2 3/2023 Siess et al.
11,616,397 B2 3/2023 Schilling
11,628,293 B2 4/2023 Gandhi et al.
11,639,722 B2 5/2023 Medvedev et al.
11,642,512 B2 5/2023 Schilling
11,648,386 B2 5/2023 Poirer
11,653,841 B2 5/2023 Reyes et al.
11,666,746 B2 6/2023 Ferrari et al.
11,674,517 B2 6/2023 Mohl
11,676,718 B2 6/2023 Agnello et al.
11,682,924 B2 6/2023 Hansen et al.
11,689,057 B2 6/2023 Hansen
11,694,539 B2 7/2023 Kudlik et al.
11,694,813 B2 7/2023 El Katerji et al.
11,696,782 B2 7/2023 Carlson et al.
11,699,551 B2 7/2023 Diekhans et al.
11,707,617 B2 7/2023 Reyes et al.
11,712,167 B2 8/2023 Medvedev et al.
11,724,091 B2 8/2023 Siess et al.
11,745,005 B2 9/2023 Delgado, III
11,752,354 B2 9/2023 Stotz et al.
11,754,077 B1 9/2023 Mohl
D1,001,145 S 10/2023 Lussier et al.
D1,001,146 S 10/2023 Lussier et al.
11,771,885 B2 10/2023 Liu et al.
11,779,234 B2 10/2023 Harjes et al.
11,781,551 B2 10/2023 Yanal et al.
11,793,994 B2 10/2023 Josephy et al.
11,804,767 B2 10/2023 Vogt et al.
11,806,116 B2 11/2023 Tuval et al.
11,806,517 B2 11/2023 Petersen
11,806,518 B2 11/2023 Michelena et al.
11,818,782 B2 11/2023 Doudian et al.
11,824,381 B2 11/2023 Conyers et al.
11,837,364 B2 12/2023 Lee et al.
11,844,592 B2 12/2023 Tuval et al.
11,850,414 B2 12/2023 Schenck et al.
D1,012,284 S 1/2024 Glaser et al.
11,872,384 B2 1/2024 Cotter
11,881,721 B2 1/2024 Araujo et al.
11,883,207 B2 1/2024 El Katerji et al.
D1,014,552 S 2/2024 Lussier et al.
11,900,660 B2 2/2024 Saito et al.
11,903,657 B2 2/2024 Geric et al.
D1,017,634 S 3/2024 Lussier et al.
D1,017,699 S 3/2024 Moore et al.
11,923,078 B2 3/2024 Fallen et al.
11,923,093 B2 3/2024 Moffitt et al.
11,925,794 B2 3/2024 Malkin et al.
11,931,588 B2 3/2024 Aghassian
11,986,274 B2 5/2024 Edelman
11,996,699 B2 5/2024 Vasconcelos Araujo et al.
12,017,076 B2 6/2024 Tan et al.
12,029,891 B2 7/2024 Siess et al.
12,059,559 B2 8/2024 Muller et al.
D1,043,730 S 9/2024 Lussier et al.
D1,043,731 S 9/2024 Lussier et al.
12,076,544 B2 9/2024 Siess et al.
12,102,835 B2 10/2024 Stotz et al.
12,144,976 B2 11/2024 Baumbach et al.
12,150,647 B2 11/2024 Schuelke et al.
12,178,554 B2 12/2024 Stotz et al.
12,179,009 B2 12/2024 El Katerji et al.
12,183,459 B2 12/2024 Agnello et al.
12,194,287 B2 1/2025 Kassel et al.
12,201,821 B2 1/2025 Schlebusch et al.
12,211,615 B2 1/2025 Nix et al.
D1,060,379 S 2/2025 Lussier et al.
12,213,771 B2 2/2025 Curran et al.
12,217,850 B2 2/2025 Agnello
12,222,267 B2 2/2025 Stotz et al.
12,230,868 B2 2/2025 Wenning et al.
12,233,250 B2 2/2025 Stotz et al.
12,251,551 B2 3/2025 Liu et al.
12,257,424 B2 3/2025 Schlebusch et al.
12,296,158 B2 5/2025 Higgins et al.
12,296,159 B2 5/2025 Schilling et al.
12,310,708 B2 5/2025 Schlebusch et al.
12,311,160 B2 5/2025 Schlebusch et al.
12,324,906 B2 6/2025 Baumbach et al.
12,329,501 B2 6/2025 Moyer et al.
12,329,956 B2 6/2025 Sunagawa
12,329,959 B2 6/2025 Hassan et al.
12,343,518 B2 7/2025 Tuval et al.
D1,090,610 S 8/2025 Kroeker et al.
12,377,256 B2 8/2025 Stotz et al.
12,390,168 B2 8/2025 Katerji et al.
12,397,099 B2 8/2025 Germain et al.
12,397,147 B2 8/2025 Siess et al.
12,400,788 B2 8/2025 Diekhans et al.
D1,092,492 S 9/2025 Lussier et al.
12,403,296 B2 9/2025 Baumbach et al.
12,409,313 B2 9/2025 Eggen et al.
12,424,306 B2 9/2025 Liu et al.
12,424,315 B2 9/2025 Nix et al.
12,434,060 B2 10/2025 Tan et al.
12,445,278 B2 10/2025 Agnello
12,451,230 B2 10/2025 El Katerji et al.
12,476,488 B2 11/2025 Araujo et al.
12,478,266 B2 11/2025 Edelman et al.
12,478,267 B2 11/2025 Schlebusch et al.
12,491,357 B2 12/2025 Baumbach et al.
12,494,292 B2 12/2025 El Katerji et al.
12,502,524 B2 12/2025 Stigloher et al.
12,508,418 B2 12/2025 Baumbach et al.
12,521,543 B2 1/2026 Egler
12,544,556 B2 2/2026 Tuval et al.
12,544,557 B2 2/2026 Lee et al.
12,544,559 B2 2/2026 Barry
2001/0016686 A1 8/2001 Okada et al.
2001/0037093 A1 11/2001 Benkowski et al.
2001/0039828 A1 11/2001 Shin et al.
2002/0022785 A1 2/2002 Romano
2002/0093412 A1 7/2002 Morrison
2002/0147495 A1 10/2002 Petroff
2002/0151761 A1 10/2002 Viole et al.
2002/0177324 A1 11/2002 Metzler
2003/0040765 A1 2/2003 Breznock
2003/0069465 A1 4/2003 Benkowski et al.
2003/0125766 A1 7/2003 Ding
2003/0130581 A1 7/2003 Salo et al.
2003/0139643 A1 7/2003 Smith et al.
2003/0167002 A1 9/2003 Nagar et al.
2003/0191357 A1 10/2003 Frazier
2003/0199727 A1 10/2003 Burke
2004/0022640 A1 2/2004 Siess et al.
2004/0034411 A1 2/2004 Quijano
2004/0044266 A1 3/2004 Siess et al.
2004/0065143 A1 4/2004 Husher
2004/0124979 A1 7/2004 Medema
2004/0130009 A1 7/2004 Tangpuz
2004/0167376 A1 8/2004 Peters et al.
2004/0167410 A1 8/2004 Hettrick
2004/0225177 A1 11/2004 Coleman et al.
2004/0260346 A1 12/2004 Overall et al.
2005/0001324 A1 1/2005 Dunn
2005/0006083 A1 1/2005 Chen et al.
2005/0019167 A1 1/2005 Nusser et al.

(56) References Cited

U.S. PATENT DOCUMENTS

2005/0046044 A1 3/2005 Theuss
2005/0107658 A1 5/2005 Brockway
2005/0107847 A1 5/2005 Gruber et al.
2005/0126268 A1 6/2005 Ouriev et al.
2005/0267322 A1 12/2005 LaRose
2006/0004423 A1 1/2006 Boveja et al.
2006/0030809 A1 2/2006 Barzilay et al.
2006/0108697 A1 5/2006 Wang
2006/0108901 A1 5/2006 Mao-Chin et al.
2006/0122583 A1 6/2006 Pesach et al.
2006/0190036 A1 8/2006 Wendel et al.
2006/0196277 A1 9/2006 Allen et al.
2006/0217785 A1 9/2006 Matei
2006/0229488 A1 10/2006 Ayre et al.
2006/0287600 A1 12/2006 McEowen
2006/0287604 A1 12/2006 Hickey
2007/0060787 A1 3/2007 Peters et al.
2007/0069354 A1 3/2007 Dangelmaier
2007/0088214 A1 4/2007 Shuros et al.
2007/0129767 A1 6/2007 Wahlstrand
2007/0156006 A1 7/2007 Smith et al.
2007/0266778 A1 11/2007 Corey et al.
2007/0282209 A1 12/2007 Lui et al.
2008/0015481 A1 1/2008 Bergin et al.
2008/0079392 A1 4/2008 Baarman et al.
2008/0082005 A1 4/2008 Stern et al.
2008/0097595 A1 4/2008 Gabbay
2008/0102096 A1 5/2008 Molin et al.
2008/0108901 A1 5/2008 Baba et al.
2008/0108930 A1 5/2008 Weitzel et al.
2008/0133006 A1 6/2008 Crosby et al.
2008/0146996 A1 6/2008 Smisson
2008/0210016 A1 9/2008 Zwirn et al.
2008/0211455 A1 9/2008 Park et al.
2008/0238364 A1 10/2008 Weber
2008/0248614 A1 10/2008 Yang
2008/0262361 A1 10/2008 Gutfinger et al.
2008/0266922 A1 10/2008 Mumtaz et al.
2008/0275339 A1 11/2008 Thiemann et al.
2008/0287799 A1 11/2008 Hall
2008/0306328 A1 12/2008 Ercolani
2009/0004037 A1 1/2009 Ito
2009/0010462 A1 1/2009 Ekchian et al.
2009/0024042 A1 1/2009 Nunez et al.
2009/0064755 A1 3/2009 Fleischli et al.
2009/0105799 A1 4/2009 Hekmat et al.
2009/0131765 A1 5/2009 Roschak et al.
2009/0134711 A1 5/2009 Issa et al.
2009/0198307 A1 8/2009 Mi et al.
2009/0198312 A1 8/2009 Barker
2009/0212637 A1 8/2009 Baarman et al.
2009/0226328 A1 9/2009 Morello
2009/0276016 A1 11/2009 Phillips et al.
2009/0312650 A1 12/2009 Maile et al.
2010/0010354 A1 1/2010 Skerl et al.
2010/0010582 A1 1/2010 Carbunaru
2010/0082099 A1 4/2010 Vodermayer et al.
2010/0087742 A1 4/2010 Bishop et al.
2010/0191035 A1 7/2010 Kang et al.
2010/0219967 A1* 9/2010 Kaufmann ........... H04B 17/318
340/686.6
2010/0222632 A1 9/2010 Poirier
2010/0222633 A1 9/2010 Poirier
2010/0222635 A1 9/2010 Poirier
2010/0222878 A1 9/2010 Poirier
2010/0268017 A1 10/2010 Siess
2010/0280568 A1 11/2010 Bulkes et al.
2010/0298625 A1 11/2010 Reichenbach et al.
2010/0312310 A1 12/2010 Meskens
2010/0331918 A1 12/2010 Digiore et al.
2010/0331920 A1 12/2010 Digiore et al.
2011/0004278 A1 1/2011 Aghassian
2011/0022057 A1 1/2011 Eigler et al.
2011/0034874 A1 2/2011 Reitan
2011/0071336 A1* 3/2011 Yomtov ............. A61M 60/873
600/16
2011/0137394 A1 6/2011 Lunsford et al.
2011/0144744 A1 6/2011 Wampler
2011/0160516 A1 6/2011 Dague
2011/0172505 A1 7/2011 Kim
2011/0184301 A1 7/2011 Holmstrom
2011/0186943 A1 8/2011 Pahl
2011/0196452 A1 8/2011 Forsell
2011/0218435 A1 9/2011 Srinivasan et al.
2011/0224720 A1 9/2011 Kassab et al.
2011/0230068 A1 9/2011 Pahl
2012/0019201 A1 1/2012 Peterson
2012/0022645 A1 1/2012 Burke
2012/0029408 A1 2/2012 Beaudin
2012/0050931 A1 3/2012 Terry et al.
2012/0068691 A1 3/2012 Ejury
2012/0084024 A1 4/2012 Norcross, Jr.
2012/0112543 A1 5/2012 Van Wageningen et al.
2012/0150291 A1 6/2012 Aber
2012/0158074 A1 6/2012 Hall
2012/0197141 A1 8/2012 Vanney
2012/0203476 A1 8/2012 Dam
2012/0212178 A1 8/2012 Kim
2012/0235633 A1 9/2012 Kesler et al.
2012/0245404 A1 9/2012 Smith
2012/0247200 A1 10/2012 Ahonen et al.
2012/0310037 A1 12/2012 Choi et al.
2012/0330214 A1 12/2012 Peters et al.
2013/0041204 A1 2/2013 Heilman et al.
2013/0046129 A1 2/2013 Medvedev et al.
2013/0066141 A1 3/2013 Doerr et al.
2013/0069651 A1 3/2013 Lumiani
2013/0072846 A1 3/2013 Heide et al.
2013/0099585 A1 4/2013 Von Novak et al.
2013/0116575 A1 5/2013 Mickle et al.
2013/0178915 A1 7/2013 Radziemski
2013/0280692 A1 10/2013 Gourlay
2013/0289334 A1* 10/2013 Badstibner .............. H01F 38/14
307/104
2013/0303831 A1 11/2013 Evans
2013/0303970 A1 11/2013 Keenan et al.
2013/0304404 A1 11/2013 Dam
2014/0012282 A1 1/2014 Fritsch
2014/0028107 A1 1/2014 Kwon
2014/0030122 A1 1/2014 Ozaki
2014/0039587 A1 2/2014 Romero
2014/0063666 A1 3/2014 Kallal et al.
2014/0094645 A1 4/2014 Lafontaine et al.
2014/0100414 A1 4/2014 Tamez et al.
2014/0104898 A1 4/2014 Yeo et al.
2014/0107754 A1 4/2014 Fuhs et al.
2014/0114202 A1 4/2014 Hein et al.
2014/0128659 A1 5/2014 Heuring et al.
2014/0135884 A1 5/2014 Tockman et al.
2014/0194058 A1 7/2014 Lee et al.
2014/0200389 A1 7/2014 Yanai et al.
2014/0233184 A1 8/2014 Thompson et al.
2014/0243688 A1 8/2014 Caron et al.
2014/0249603 A1 9/2014 Yan et al.
2014/0265620 A1 9/2014 Hoarau et al.
2014/0275720 A1 9/2014 Ferrari
2014/0275727 A1* 9/2014 Bonde ................ A61M 60/178
600/16
2014/0296677 A1 10/2014 McEowen
2014/0303426 A1 10/2014 Kerkhoffs et al.
2014/0342203 A1 11/2014 Elian
2014/0346884 A1 11/2014 Fujita
2015/0008755 A1 1/2015 Sone
2015/0027224 A1 1/2015 Schiffer
2015/0028805 A1 1/2015 Dearden et al.
2015/0032007 A1 1/2015 Ottevanger et al.
2015/0080743 A1 3/2015 Siess
2015/0090372 A1 4/2015 Branagan et al.
2015/0141832 A1 5/2015 Yu et al.
2015/0157216 A1 6/2015 Stigall et al.
2015/0196076 A1 7/2015 Billingslea
2015/0200562 A1 7/2015 Kilinc et al.
2015/0201900 A1 7/2015 Syed

(56) References Cited

U.S. PATENT DOCUMENTS

2015/0244166 A1 8/2015 Chen
2015/0250935 A1 9/2015 Anderson et al.
2015/0290372 A1 10/2015 Muller et al.
2015/0290373 A1 10/2015 Rudser et al.
2015/0306290 A1 10/2015 Rosenberg et al.
2015/0306291 A1 10/2015 Bonde et al.
2015/0307344 A1 10/2015 Ernst
2015/0327921 A1 11/2015 Govari
2015/0333532 A1 11/2015 Han et al.
2015/0380972 A1 12/2015 Fort
2016/0000983 A1 1/2016 Mohl et al.
2016/0008531 A1 1/2016 Wang et al.
2016/0022889 A1 1/2016 Bluvshtein
2016/0022890 A1 1/2016 Schwammenthal et al.
2016/0045165 A1 2/2016 Braido et al.
2016/0067395 A1 3/2016 Jimenez et al.
2016/0081680 A1 3/2016 Taylor
2016/0087558 A1 3/2016 Yamamoto
2016/0095968 A1* 4/2016 Rudser ................ A61M 60/523 600/16
2016/0101230 A1 4/2016 Ochsner et al.
2016/0151553 A1 6/2016 Bonde
2016/0166747 A1 6/2016 Frazier et al.
2016/0175501 A1 6/2016 Schuermann
2016/0213828 A1 7/2016 Sievers
2016/0226296 A1 8/2016 Bae
2016/0250399 A1 9/2016 Tiller et al.
2016/0268846 A1 9/2016 Akuzawa et al.
2016/0271309 A1 9/2016 Throckmorton et al.
2016/0278856 A1 9/2016 Panescu
2016/0302672 A1 10/2016 Kuri
2016/0303299 A1 10/2016 Muller
2016/0317043 A1 11/2016 Campo
2016/0331980 A1 11/2016 Strommer et al.
2016/0336811 A1 11/2016 Liu
2016/0344302 A1 11/2016 Inoue
2017/0010144 A1 1/2017 Lenner et al.
2017/0018967 A1 1/2017 Berkhout
2017/0043170 A1 2/2017 Guardiani
2017/0047781 A1 2/2017 Stanislawski et al.
2017/0070082 A1 3/2017 Zheng et al.
2017/0112985 A1 4/2017 Yomtov
2017/0136164 A1 5/2017 Yeatts
2017/0143977 A1 5/2017 Kaib et al.
2017/0202575 A1 7/2017 Stanfield et al.
2017/0203104 A1 7/2017 Nageri et al.
2017/0224279 A1 8/2017 Cahan et al.
2017/0231717 A1 8/2017 Forsell
2017/0239407 A1 8/2017 Hayward
2017/0258980 A1 9/2017 Katsuki et al.
2017/0258981 A1 9/2017 Franano
2017/0271919 A1 9/2017 Von Novak, III et al.
2017/0275799 A1 9/2017 Chen
2017/0288448 A1 10/2017 Kranz et al.
2017/0303375 A1 10/2017 Woodhead
2017/0340789 A1 11/2017 Bonde et al.
2017/0347229 A1* 11/2017 Kwon .................... H04W 4/80
2017/0348470 A1 12/2017 D'Ambrosio et al.
2017/0353053 A1 12/2017 Muratov
2017/0354812 A1 12/2017 Callaghan et al.
2017/0361115 A1 12/2017 Aghassian
2017/0361117 A1 12/2017 Aghassian
2018/0021497 A1 1/2018 Nunez
2018/0064860 A1 3/2018 Nunez et al.
2018/0078159 A1 3/2018 Edelman et al.
2018/0078329 A1 3/2018 Hansen et al.
2018/0093070 A1 4/2018 Cottone
2018/0110910 A1 4/2018 Rodemerk et al.
2018/0126053 A1 5/2018 Zilbershlag et al.
2018/0194236 A1 7/2018 Elshaer et al.
2018/0207336 A1 7/2018 Solem
2018/0250457 A1 9/2018 Morello et al.
2018/0256796 A1 9/2018 Hansen
2018/0256800 A1 9/2018 Conyers
2018/0269724 A1 9/2018 Smith
2018/0269930 A1 9/2018 Kwon
2018/0278099 A1 9/2018 Hong
2018/0280598 A1 10/2018 Curran et al.
2018/0280708 A1 10/2018 Escalona et al.
2018/0287405 A1 10/2018 Govindaraj
2018/0316209 A1* 11/2018 Gliner .................. H02J 50/402
2018/0326131 A1 11/2018 Muller et al.
2018/0333059 A1 11/2018 Casas
2018/0353667 A1 12/2018 Moyer et al.
2018/0369469 A1 12/2018 Le Duc De Lillers et al.
2019/0001038 A1 1/2019 Yomtov et al.
2019/0004037 A1 1/2019 Zhang et al.
2019/0060543 A1 2/2019 Khanal et al.
2019/0068004 A1 2/2019 Louis
2019/0074726 A1 3/2019 Hosotani
2019/0097447 A1 3/2019 Partovi
2019/0120905 A1 4/2019 Wong
2019/0175808 A1 6/2019 Zilbershlag et al.
2019/0192752 A1 6/2019 Tiller et al.
2019/0192753 A1 6/2019 Liu et al.
2019/0209755 A1 7/2019 Nix et al.
2019/0209758 A1 7/2019 Tuval et al.
2019/0216995 A1 7/2019 Kapur et al.
2019/0217002 A1 7/2019 Urakabe
2019/0222064 A1 7/2019 Du et al.
2019/0223877 A1 7/2019 Nitzen et al.
2019/0231523 A1 8/2019 Lombardi
2019/0240680 A1 8/2019 Hayakawa
2019/0254543 A1 8/2019 Hartholt et al.
2019/0267913 A1 8/2019 Lim
2019/0282741 A1 9/2019 Franano et al.
2019/0282744 A1 9/2019 D'Ambrosio et al.
2019/0305613 A1 10/2019 Oshima
2019/0344000 A1 11/2019 Kushwaha et al.
2019/0351118 A1 11/2019 Graichen et al.
2019/0351120 A1 11/2019 Kushwaha et al.
2019/0393735 A1 12/2019 Lee et al.
2020/0016309 A1 1/2020 Kallenbach et al.
2020/0022811 A1 1/2020 Griswold
2020/0023109 A1 1/2020 Epple
2020/0028376 A1 1/2020 Ha
2020/0038567 A1 2/2020 Siess et al.
2020/0054806 A1 2/2020 Sun
2020/0060559 A1 2/2020 Edelman et al.
2020/0069857 A1 3/2020 Schwammenthal et al.
2020/0136421 A1 4/2020 Kim
2020/0139032 A1 5/2020 Bryson et al.
2020/0227954 A1 7/2020 Ding et al.
2020/0253583 A1 8/2020 Brisken et al.
2020/0312450 A1 10/2020 Agnello et al.
2020/0350812 A1 11/2020 Vogt et al.
2020/0366121 A1 11/2020 Guedon
2020/0373768 A1 11/2020 Danilovic
2021/0052793 A1 2/2021 Struthers et al.
2021/0057804 A1 2/2021 Wenning
2021/0143688 A1 5/2021 Agrawal et al.
2021/0268264 A1 9/2021 Stotz
2021/0290087 A1 9/2021 Schlebusch
2021/0290930 A1 9/2021 Kasel
2021/0290931 A1 9/2021 Baumbach
2021/0290933 A1 9/2021 Stotz
2021/0290939 A1 9/2021 Baumbach
2021/0298653 A1 9/2021 Woodard
2021/0322011 A1 10/2021 Schuelke et al.
2021/0336484 A1 10/2021 Araujo et al.
2021/0339002 A1 11/2021 Schlebusch et al.
2021/0346674 A1 11/2021 Baumbach et al.
2021/0346675 A1 11/2021 Schlebusch et al.
2021/0346676 A1 11/2021 Schlebusch et al.
2021/0346677 A1 11/2021 Baumbach et al.
2021/0346678 A1 11/2021 Baumbach et al.
2021/0378523 A1 12/2021 Budde
2021/0379359 A1 12/2021 Schellenberg
2021/0379360 A1 12/2021 Schellenberg
2021/0386990 A1 12/2021 Stotz et al.
2021/0399582 A1 12/2021 Araujo et al.
2022/0032032 A1 2/2022 Schlebusch et al.
2022/0032036 A1 2/2022 Baumbach et al.
2022/0039669 A1 2/2022 Schlebusch et al.

(56) References Cited

U.S. PATENT DOCUMENTS

| | | | |
|---|---|---|---|
| 2022/0047173 | A1 | 2/2022 | Stotz et al. |
| 2022/0050037 | A1 | 2/2022 | Stotz et al. |
| 2022/0076807 | A1 | 3/2022 | Agnello |
| 2022/0079457 | A1 | 3/2022 | Tuval et al. |
| 2022/0080184 | A1 | 3/2022 | Clifton et al. |
| 2022/0080185 | A1 | 3/2022 | Clifton et al. |
| 2022/0103023 | A1 | 3/2022 | Govindaraj |
| 2022/0126085 | A1 | 4/2022 | Farnan |
| 2022/0126086 | A1 | 4/2022 | Schlebusch et al. |
| 2022/0142462 | A1 | 5/2022 | Douk et al. |
| 2022/0161019 | A1 | 5/2022 | Mitze et al. |
| 2022/0161021 | A1 | 5/2022 | Mitze et al. |
| 2022/0166253 | A1 | 5/2022 | Forsell |
| 2022/0320901 | A1 | 10/2022 | Araujo et al. |
| 2022/0361762 | A1 | 11/2022 | Lalancette |
| 2022/0417673 | A1 | 12/2022 | Narampanawe |
| 2023/0145482 | A1 | 5/2023 | Garrigue |
| 2023/0173250 | A1 | 6/2023 | Stigloher |
| 2023/0191141 | A1 | 6/2023 | Wenning et al. |
| 2023/0258694 | A1 | 8/2023 | Vijayakumar |
| 2023/0352236 | A1 | 11/2023 | Diekhans et al. |
| 2023/0381526 | A1 | 11/2023 | Stotz et al. |
| 2024/0074828 | A1 | 3/2024 | Wenning |
| 2024/0186828 | A1 | 6/2024 | Chu |
| 2024/0269459 | A1 | 8/2024 | Schellenberg et al. |
| 2024/0312433 | A1 | 9/2024 | Kim |
| 2025/0032773 | A1 | 1/2025 | Baumbach et al. |
| 2025/0121177 | A1 | 4/2025 | West |
| 2025/0134652 | A1 | 5/2025 | Maiorano |
| 2025/0143587 | A1 | 5/2025 | Stotz |
| 2025/0144397 | A1 | 5/2025 | Kassel et al. |
| 2025/0222247 | A1 | 7/2025 | Schlebusch |
| 2025/0235687 | A1 | 7/2025 | Schlebusch et al. |
| 2025/0251330 | A1 | 8/2025 | Stotz |
| 2025/0281060 | A1 | 9/2025 | Schlebusch et al. |
| 2025/0319299 | A1 | 10/2025 | Stotz et al. |
| 2025/0345590 | A1 | 11/2025 | Schlebusch et al. |
| 2025/0367429 | A1 | 12/2025 | Eggen et al. |
| 2025/0367431 | A1 | 12/2025 | Baumbach et al. |
| 2026/0048254 | A1 | 2/2026 | Scheffler et al. |

FOREIGN PATENT DOCUMENTS

| | | | |
|---|---|---|---|
| CN | 1192351 | A | 9/1998 |
| CN | 1222862 | A | 7/1999 |
| CN | 1202871 | C | 5/2005 |
| CN | 1661338 | A | 8/2005 |
| CN | 101128168 | | 2/2008 |
| CN | 101208045 | | 6/2008 |
| CN | 101214158 | | 7/2008 |
| CN | 101351237 | | 1/2009 |
| CN | 101448535 | | 6/2009 |
| CN | 101460094 | | 6/2009 |
| CN | 101579233 | | 11/2009 |
| CN | 201437016 | | 4/2010 |
| CN | 101711683 | | 5/2010 |
| CN | 201658687 | | 12/2010 |
| CN | 102421372 | | 4/2012 |
| CN | 102803923 | | 11/2012 |
| CN | 103143072 | | 6/2013 |
| CN | 103328018 | | 9/2013 |
| CN | 103857326 | | 6/2014 |
| CN | 103942511 | | 7/2014 |
| CN | 103957957 | | 7/2014 |
| CN | 104105449 | | 10/2014 |
| CN | 104188687 | | 12/2014 |
| CN | 104274873 | | 1/2015 |
| CN | 106104229 | | 11/2016 |
| CN | 106333707 | | 1/2017 |
| CN | 104888293 | | 3/2017 |
| CN | 206007680 | | 3/2017 |
| CN | 106776441 | | 5/2017 |
| CN | 107530479 | | 1/2018 |
| CN | 107632167 | | 1/2018 |
| CN | 109939282 | | 6/2019 |
| CN | 209790495 | | 12/2019 |
| CN | 210020563 | | 2/2020 |
| CN | 112168427 | | 1/2021 |
| CN | 215841206 | | 2/2022 |
| CN | 114886614 | | 8/2022 |
| CN | 217828630 | | 11/2022 |
| CN | 115916111 | | 4/2023 |
| CN | 116271502 | | 6/2023 |
| CN | 117959584 | | 5/2024 |
| CN | 113769260 | | 9/2024 |
| CN | 118717356 | | 10/2024 |
| CN | 118920928 | | 11/2024 |
| CN | 119033506 | | 11/2024 |
| DE | 11 65 144 | | 3/1964 |
| DE | 195 20 920 | | 12/1995 |
| DE | 198 21 307 | | 10/1999 |
| DE | 100 59 714 | | 5/2002 |
| DE | 100 60 275 | | 6/2002 |
| DE | 103 02 550 | | 8/2004 |
| DE | 20 2005 020 288 | | 6/2007 |
| DE | 10 2006 001 180 | | 9/2007 |
| DE | 10 2009 007 216 | | 8/2010 |
| DE | 10 2009 025 464 | | 1/2011 |
| DE | 10 2011 106 142 | | 12/2012 |
| DE | 10 2012 200 912 | | 7/2013 |
| DE | 20 2011 110 389 | | 9/2013 |
| DE | 11 2012 005 944 | | 12/2014 |
| DE | 20 2013 007 408 | | 12/2014 |
| DE | 10 2015 004 177 | | 10/2015 |
| DE | 10 2016 106 683 | | 10/2016 |
| DE | 10 2015 222 199 | | 5/2017 |
| DE | 10 2016 225 862 | | 6/2017 |
| DE | 20 2015 009 422 | | 7/2017 |
| DE | 10 2016 203 172 | | 8/2017 |
| DE | 10 2012 207 042 | | 9/2017 |
| DE | 10 2016 013 334 | | 4/2018 |
| DE | 10 2017 213 475 | | 2/2019 |
| DE | 10 2018 204 604 | | 10/2019 |
| DE | 10 2018 204 610 | | 10/2019 |
| DE | 10 2018 206 714 | | 11/2019 |
| DE | 10 2018 206 724 | | 11/2019 |
| DE | 10 2018 206 725 | | 11/2019 |
| DE | 10 2018 206 727 | | 11/2019 |
| DE | 10 2018 206 731 | | 11/2019 |
| DE | 10 2018 206 750 | | 11/2019 |
| DE | 10 2018 206 754 | | 11/2019 |
| DE | 10 2018 206 758 | | 11/2019 |
| DE | 10 2018 208 945 | | 12/2019 |
| DE | 10 2018 222 505 | | 6/2020 |
| DE | 10 2020 102 473 | | 8/2021 |
| EP | 0 794 411 | | 9/1997 |
| EP | 0 916 359 | | 5/1999 |
| EP | 0 930 086 | | 7/1999 |
| EP | 1 062 959 | | 12/2000 |
| EP | 1 339 443 | | 11/2001 |
| EP | 1 011 803 | | 9/2004 |
| EP | 1 354 606 | | 6/2006 |
| EP | 2 143 385 | | 1/2010 |
| EP | 2 175 770 | | 4/2010 |
| EP | 2 187 807 | | 6/2012 |
| EP | 2 570 143 | | 3/2013 |
| EP | 2 401 003 | | 10/2013 |
| EP | 2 752 209 | | 7/2014 |
| EP | 2 782 210 | | 9/2014 |
| EP | 1 871 441 | | 11/2014 |
| EP | 2 859 911 | | 4/2015 |
| EP | 2 966 753 | | 1/2016 |
| EP | 2 835 141 | | 8/2016 |
| EP | 2 454 799 | | 9/2016 |
| EP | 3 088 016 | | 11/2016 |
| EP | 2 585 129 | | 3/2017 |
| EP | 2 709 689 | | 4/2017 |
| EP | 3 220 505 | | 9/2017 |
| EP | 2 136 861 | | 12/2017 |
| EP | 3 020 426 | | 12/2017 |
| EP | 3 287 154 | | 2/2018 |
| EP | 3 205 360 | | 8/2018 |
| EP | 3 378 421 | | 9/2018 |
| EP | 3 389 738 | | 8/2019 |

(56) References Cited

FOREIGN PATENT DOCUMENTS

| | | |
|---|---|---|
| EP | 3 536 360 | 9/2019 |
| EP | 3 720 520 | 10/2020 |
| EP | 3 357 523 | 1/2021 |
| EP | 3 423 126 | 2/2021 |
| EP | 3 490 628 | 2/2021 |
| EP | 3 198 677 | 3/2021 |
| EP | 3 248 647 | 3/2021 |
| EP | 3 436 106 | 3/2021 |
| EP | 3 509 661 | 3/2021 |
| EP | 3 515 523 | 3/2021 |
| EP | 3 528 863 | 3/2021 |
| EP | 4 271 461 | 3/2021 |
| EP | 3 436 105 | 4/2021 |
| EP | 3 116 407 | 5/2021 |
| EP | 3 131 600 | 6/2021 |
| EP | 3 131 615 | 6/2021 |
| EP | 3 827 876 | 6/2021 |
| EP | 2 608 731 | 7/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 077 018 | 10/2021 |
| EP | 3 485 936 | 10/2021 |
| EP | 3 164 168 | 12/2021 |
| EP | 3 539 613 | 2/2022 |
| EP | 2 858 718 | 3/2022 |
| EP | 3 624 867 | 3/2022 |
| EP | 3 651 822 | 3/2022 |
| EP | 3 737 436 | 3/2022 |
| EP | 3 755 237 | 4/2022 |
| EP | 3 984 589 | 4/2022 |
| EP | 3 497 775 | 7/2022 |
| EP | 3 737 310 | 7/2022 |
| EP | 3 711 788 | 8/2022 |
| EP | 2 654 883 | 9/2022 |
| EP | 3 485 819 | 9/2022 |
| EP | 3 694 573 | 9/2022 |
| EP | 3 600 477 | 10/2022 |
| EP | 3 808 408 | 11/2022 |
| EP | 3 858 422 | 11/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 946 511 | 4/2023 |
| EP | 3 685 562 | 5/2023 |
| EP | 3 826 104 | 5/2023 |
| EP | 3 397 298 | 7/2023 |
| EP | 3 809 959 | 7/2023 |
| EP | 2 961 984 | 9/2023 |
| EP | 3 352 808 | 9/2023 |
| EP | 4 052 754 | 10/2023 |
| EP | 3 157 596 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 782 695 | 3/2024 |
| EP | 3 854 448 | 3/2024 |
| EP | 4 140 532 | 5/2024 |
| EP | 3 854 444 | 9/2024 |
| EP | 3 809 960 | 12/2024 |
| EP | 3 854 446 | 2/2025 |
| EP | 3 970 785 | 3/2025 |
| EP | 3 899 964 | 6/2025 |
| EP | 3 948 888 | 6/2025 |
| EP | 3 965 845 | 6/2025 |
| EP | 4 039 319 | 6/2025 |
| EP | 4 297 672 | 7/2025 |
| EP | 3 668 559 | 8/2025 |
| EP | 3 848 088 | 8/2025 |
| EP | 4 213 716 | 10/2025 |
| EP | 3 911 227 | 1/2026 |
| EP | 4 201 467 | 1/2026 |
| ES | 2 913 485 | 6/2022 |
| GB | 2 504 177 | 1/2014 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-505766 | 6/1998 |
| JP | H11-178249 | 7/1999 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-503495 | 2/2010 |
| JP | 2010-518907 | 6/2010 |
| JP | 4706886 | 6/2011 |
| JP | 2012-520157 | 9/2012 |
| JP | 2013-013216 | 1/2013 |
| JP | 2013-128792 | 7/2013 |
| JP | 2015-514531 | 5/2015 |
| JP | 2015-515429 | 5/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2018-046708 | 3/2018 |
| JP | 2019-508128 | 3/2019 |
| JP | 2019-523110 | 8/2019 |
| JP | 2020-072985 | 5/2020 |
| JP | 2019-509141 | 2/2022 |
| KR | 10-1185112 | 9/2012 |
| WO | WO 89/006513 | 1/1989 |
| WO | WO 92/015239 | 9/1992 |
| WO | WO 94/009835 | 5/1994 |
| WO | WO 98/043688 | 10/1998 |
| WO | WO 2006/122001 | 11/2006 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |
| WO | WO 2010/142286 | 12/2010 |
| WO | WO 2010/143272 | 12/2010 |

(56) References Cited

FOREIGN PATENT DOCUMENTS

WO WO 2011/007300 1/2011
WO WO 2012/018917 2/2012
WO WO 2012/112378 8/2012
WO WO 2012/147061 11/2012
WO WO 2013/160443 10/2013
WO WO 2013/164831 11/2013
WO WO 2014/042925 3/2014
WO WO 2014/141284 9/2014
WO WO 2014/165635 10/2014
WO WO 2015/085220 6/2015
WO WO 2015/152732 10/2015
WO WO 2016/001284 1/2016
WO WO 2016/066180 5/2016
WO WO 2016/137743 9/2016
WO WO 2017/021846 2/2017
WO WO 2017/032751 3/2017
WO WO 2017/060257 4/2017
WO WO 2017/066257 4/2017
WO WO 2017/089440 6/2017
WO WO 2017/106190 6/2017
WO WO 2017/118738 7/2017
WO WO 2017/147291 8/2017
WO WO 2017/165372 9/2017
WO WO 2017/213032 12/2017
WO WO 2017/214118 12/2017
WO WO 2017/218349 12/2017
WO WO 2018/005228 1/2018
WO WO 2018/033799 2/2018
WO WO 2018/048800 3/2018
WO WO 2018/078615 5/2018
WO WO 2018/100192 6/2018
WO WO 2018/109038 6/2018
WO WO 2019/013794 1/2019
WO WO 2019/025258 2/2019
WO WO 2019/025259 2/2019
WO WO 2019/025260 2/2019
WO WO 2019/034670 2/2019
WO WO 2019/034775 2/2019
WO WO 2019/078723 4/2019
WO WO 2019/101786 5/2019
WO WO 2019/118371 6/2019
WO WO 2019/126721 6/2019
WO WO 2019/137911 7/2019
WO WO 2019/145253 8/2019
WO WO 2019/158996 8/2019
WO WO 2019/183247 9/2019
WO WO 2019/185511 10/2019
WO WO 2019/185512 10/2019
WO WO 2019/193604 10/2019
WO WO 2019/211400 11/2019
WO WO 2019/211405 11/2019
WO WO 2019/211410 11/2019
WO WO 2019/211413 11/2019
WO WO 2019/211414 11/2019
WO WO 2019/211415 11/2019
WO WO 2019/211416 11/2019
WO WO 2019/219883 11/2019
WO WO 2019/229210 12/2019
WO WO 2019/229220 12/2019
WO WO 2019/229224 12/2019
WO WO 2019/234145 12/2019
WO WO 2019/234148 12/2019
WO WO 2019/234149 12/2019
WO WO 2019/234151 12/2019
WO WO 2019/234152 12/2019
WO WO 2019/234153 12/2019
WO WO 2019/234161 12/2019
WO WO 2019/234162 12/2019
WO WO 2019/234163 12/2019
WO WO 2019/234164 12/2019
WO WO 2019/234166 12/2019
WO WO 2019/234167 12/2019
WO WO 2019/234169 12/2019
WO WO 2019/241556 12/2019
WO WO 2019/243582 12/2019
WO WO 2019/244031 12/2019
WO WO 2020/030686 2/2020
WO WO 2020/030706 2/2020
WO WO 2020/064707 4/2020
WO WO 2020/089429 5/2020
WO WO 2020/198280 10/2020
WO WO 2020/243756 12/2020
WO WO 2021/159001 8/2021
WO WO 2023/040546 12/2021
WO WO 2022/074136 4/2022
WO WO 2022/109590 5/2022
WO WO 2023/226779 9/2022
WO WO 2023/037162 3/2023
WO WO 2023/076869 5/2023
WO WO 2023/112044 6/2023

OTHER PUBLICATIONS

Thoratec Corporation, "Heartmate 3™ Left Ventricular Assist System, Instructions for Use;" Document: 10006135.B, Publication Date: Aug. 2017 (Year: 2017).*

Hertz Ph.D. et al, "Ultrasonic Engineering in Heart Diagnosis", The American Journal of Cardiology, Jan. 1967, vol. 19, No. 1, pp. 6-17.

International Search Report and Written Opinion received in PCT Application No. PCT/EP2019/079905, dated Feb. 4, 2020 in 20 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

(56) References Cited

OTHER PUBLICATIONS

International Preliminary Report on Patentability and Written Opinion received in PCT Application No. PCT/EP2019/079905, dated Mar. 16, 2021 in 19 pages.

Chung et al., “Improved Efficiency Characteristics of Wireless Power Charging System for Superconducting MAGLEV Train Using Inserted Permanent Magnets,” 2018 IEEE International Symposium on Electromagnetic Compatibility, 2018, pp. 564-567.

“ECG Electrodes product comparison chart,” 3M.com, 2018, https://multimedia.3m.com/mws/media/1490883O/red-dot-ecg-electrodes-comparison-chart.pdf, accessed May 18, 2025, 1 page.

Mack-Haynes, Robin, “Fasteners Made Easy,” New Mexico State University, https://pubs.nmsu.edu/_c/C232.pdf, accessed May 18, 2025, pp. 8.

Radiologyinfo.org, “Subcutaneous Port,” Definition, https://www.radiologyinfo.org/en/glossary?id=ezNFREEzNEFFLTI5OTAtNDVFNy04MkVBLTA1RDVGMDdBMzNFRHO=&i=1&b=0&modal=1, accessed Sep. 2, 2025, 1 page.

Sigg et al., “Cardiac Electophysiology Methods and Models”, Springer, Clinical Perspective: Electrophysiology in the Young and Patients with Congenital Heart Disease, Ch. 23, 2010, pp. 457-477.

Tan et al., “Surface Engineering and Patterning Using Parylene for Biological Applications.” Materials, Mar. 15, 2010, vol. 3, No. 3, pp. 1803-1832.

Walser, Eric, “Venous access ports: indications, implantation technique, follow-up, and complications;” Cardiovasc Intervent Radial, Aug. 2012; vol. 35, No. 4, pp. 751-764. (Abstract Only).

* cited by examiner

SYSTEM AND METHOD FOR CONTROLLING A CARDIAC ASSISTANCE SYSTEM

BACKGROUND

Field

The invention relates to a system for controlling a cardiac support system comprising a control device, a cardiac support system and a method for controlling said system.

Description of the Related Art

In modern cardiac support systems, also referred to as a VAD for "ventricular assist device" or a ventricular support system, a pump to support the heart function is usually implanted on or in the heart and controlled by a control device. In addition to or instead of a likewise implanted control device, a so-called extracorporeal control device can be provided, which is located outside the patient's body to enable external control.

From US 2005/0107658 A1, for example, a cardiac support system is known, which comprises both an implanted control device and an extracorporeal control device. The extracorporeal control device is wirelessly connected to the implanted control device and is used primarily for bidirectional data exchange.

SUMMARY

Based on this, the underlying object of the invention is to further improve the known systems and methods, and in particular to enable simple and rapid information acquisition as well as coordinated control, to facilitate handling, to increase user friendliness and to ensure reliable and safe operation.

With this in mind, the invention relates to a system for controlling a cardiac support system comprising a first extracorporeal control device, wherein the first control device is or can be connected to the cardiac support system with a wire or a first coil for communication and/or energy transfer. The system further comprises a second extracorporeal control device which is wirelessly connected to the first control device and/or to the cardiac support system.

A cardiac support system is in particular to be understood to be a system to support the function of a heart of a human or an animal, also referred to as an artificial heart, a ventricular assist device (VAD) or a ventricular support system. The term "extracorporeal control device" generally refers to a control device for a cardiac support system that is not intended for implantation into a body of a human or an animal, but rather is intended and configured for use outside the body. For this purpose, the extracorporeal control device in particular comprises a display and/or an input device, in particular keys or buttons or a touch-sensitive surface. A wireless connection between two devices, or between a system and a device, is in particular to be understood to mean that the two devices, or the system and the device, are configured to communicate via a wireless bidirectional data connection, in particular via a radio link. A configuration or a setup of one of the control devices can be understood here and in the following to mean that the control device comprises correspondingly required hardware components, in particular a processor and communication interfaces, and is programmed accordingly, in particular the processor. The control device can be a commercially available control device for a cardiac support system, for example, which is set up, in particular programmed, according to the invention. In the context of the invention, a wire is in particular to be understood to be a wire referred to as a "driveline," which is configured to connect the cardiac support system to the control device.

The system according to the invention has the advantage that the second extracorporeal control device provides an additional option for the user, in particular the patient or the physician, to access and gather information about the cardiac support system and also to control the cardiac support system, in particular a motor or a pump of the cardiac support system. In particular when the first extracorporeal control device is connected to the cardiac support system via the wire, i.e. the above-mentioned driveline, the not physically connected second extracorporeal control device advantageously enables a simple and rapid acquisition of information and coordinated control. Since the second control device does not have to be physically connected to any other device, it can advantageously also be handled and tucked away more discreetly. The second extracorporeal control device can furthermore be configured to be attached via a holder to a belt or other article of clothing of the patient for quick access. The flexible manageability via the second control device also advantageously allows the first extracorporeal control device to be worn as close as possible to or directly on the body, and thus reduces the distance to the implanted cardiac support system for the most reliable interaction possible. On the one hand, therefore, this advantageously increases safety and reliability, and with it also the patient's sense of security, and, on the other hand, it improves the overall comfort and user-friendliness. A control device that is not physically connected can be carried in easy reach more inconspicuously in public and is more inconspicuous to handle, so that the use of a cardiac support system is thus advantageously less conspicuous to third parties.

The second extracorporeal control device is preferably configured as a redundant unit to the first extracorporeal control device. In other words, the second extracorporeal control device is configured to take over the function of the first extracorporeal control device in the event of a failure or a malfunction of the first extracorporeal control device.

According to a particularly advantageous further development of the invention, the first control device and the second control device are structurally identical. This means in particular that the first control device and the second control device comprise the same hardware components and/or have the same structural design. The two control devices preferably also have the same exterior shape and the same exterior dimensions. This has the advantage that the first control device can easily be replaced by the second control device if necessary, for example in the event of a malfunction or a failure of the first control device as described above.

In a particularly advantageous further development of the invention, the first control device is configured as a server and the second control device is configured as a client. In other words, the two extracorporeal control devices form a network, in which the first extracorporeal control device assumes the role of the server and the second extracorporeal control device assumes the role of the client. This advantageously allows the client-server model, which has proven to be successful for networks, to be used.

In the event of an input to the first control device or to the second control device, the first control device and the second control device are preferably configured to cause the second control device or the first control device to accept the same input. If said input changes settings in the first or second control device, the same changes to the settings are then advantageously made in the second or first control device. The two control devices are thus advantageously in the same or in a synchronous state.

In a preferred further development of the invention the system comprises a first energy store for a transfer of energy via the first coil to the cardiac support system, wherein the first energy store is preferably, in particular detachably, connected to the first control device. An energy supply to the implanted cardiac support system can thus advantageously be controlled via the first extracorporeal control device. The system can preferably comprise a second energy store, which is preferably, in particular detachably, connected to the second control device. This has the advantage that the energy supply to the system as a whole is safeguarded even more.

In another advantageous configuration of the invention, the first control device and/or the second control device are configured to output an alarm signal when a minimum distance between the two control devices is exceeded. The control devices can be configured to estimate the current distance via the quality of the wireless radio links between the two control devices, for example, and compare it to the minimum distance. A strength or intensity of the signals received via the wireless connection, for example, can be used as a measure of the quality. For example, if the quality, in particular the signal strength or signal intensity, is less than a predefined minimum value, the alarm signal is triggered. The alarm signal can be emitted acoustically as a tone or tone sequence, for example, or optically via light-emitting elements of the control device or a display of the control devices. This has the advantage that the user or patient is reminded to carry both control devices.

The invention further relates to a cardiac support system comprising a system according to the invention.

The invention also relates to a method for controlling a cardiac support system, wherein the cardiac support system is controlled via a first extracorporeal control device and wherein the first control device or the cardiac support system is connected wirelessly to a second extracorporeal control device in order to control a cardiac support system. If the second control device is wirelessly connected to the first control device, the cardiac support system can be controlled by the second extracorporeal control device via the first extracorporeal control device.

With respect to the advantages of the cardiac support system according to the invention and the method according to the invention, reference is made to the corresponding advantages of the system according to the invention discussed above.

BRIEF DESCRIPTION OF THE DRAWINGS

Design examples of the invention are shown schematically in the drawings and explained in more detail in the following description. The same reference signs are used for the elements shown in the various figures, which have a similar effect, whereby a repeated description of these elements is omitted.

The figures show.

DETAILED DESCRIPTION

Figure 1:
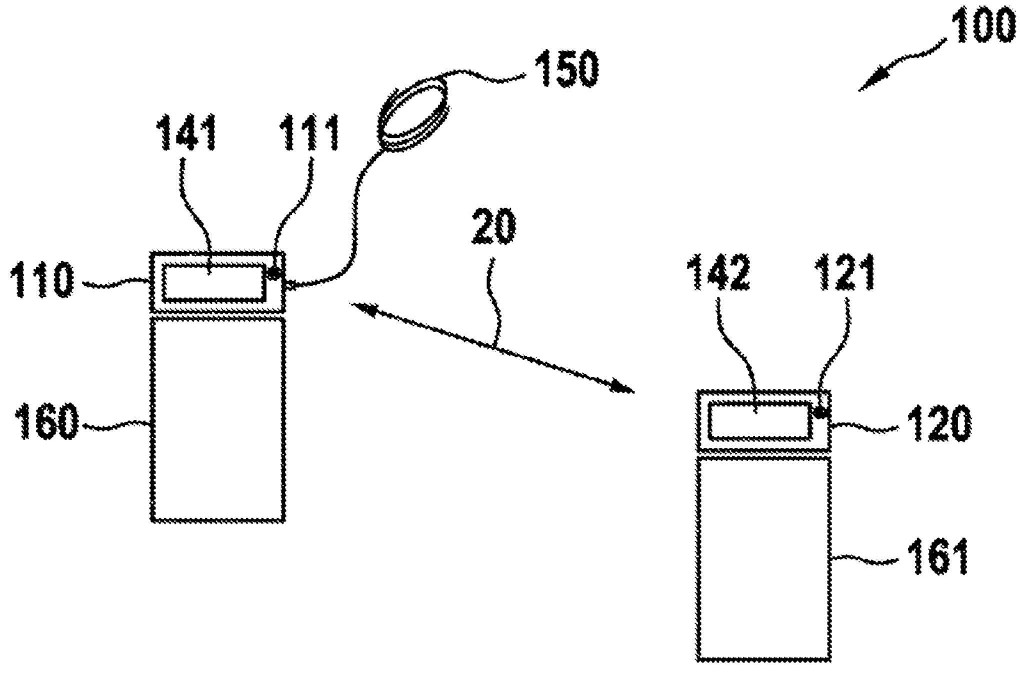
FIGS. 1 and 2 a design example of the system according to the invention and FIG. 3 a flow chart of a design example of the method according to the invention.

FIG. 1 shows a design example of the system 100 according to the invention. The system 100 comprises a first extracorporeal control device 110 and a second extracorporeal control device 120. Both control devices comprise an interface 111, 121 for wireless communication 20 with one another, for example a Bluetooth® interface 111, 121. The wireless communication takes place via radio communication according to the MedRadio or MICS (Medical Device Radiocommunications Service) specification, for example. The two control devices 110, 120 can also comprise an integrated energy source, for example a battery or an accumulator. This enables the control devices to be energy self-sufficient. The first control device 110 is connected to a coil 150 for inductive energy transfer to a cardiac support system. In addition to the possible integrated energy source, the first control device 110 also comprises a further energy source 160 for supplying energy to the cardiac support system, for example a battery or an accumulator. The further energy source 160 is preferably detachably connected to the first control device 110, for example via a latch or click mechanism. Since the second control device 120 is not physically tied to any device, the second control device 120 is characterized by a high degree of user-friendliness. To display information, the two control devices 110, 120 preferably comprise a display 141, 142, preferably a touch-sensitive display 141, 142, which is also suitable for inputting commands to the control devices 110, 120.

In this design example, the two control devices 110, 120 are structurally identical and preferably have the same structural design, so that the second control device 120 can take over the function of the first control device if necessary and is thus provided as a redundant unit to the first extracorporeal control device. For this purpose in particular, the second control device 120 can also comprise a further energy source 161 to safeguard the energy supply of the cardiac support system.

Figure 2:
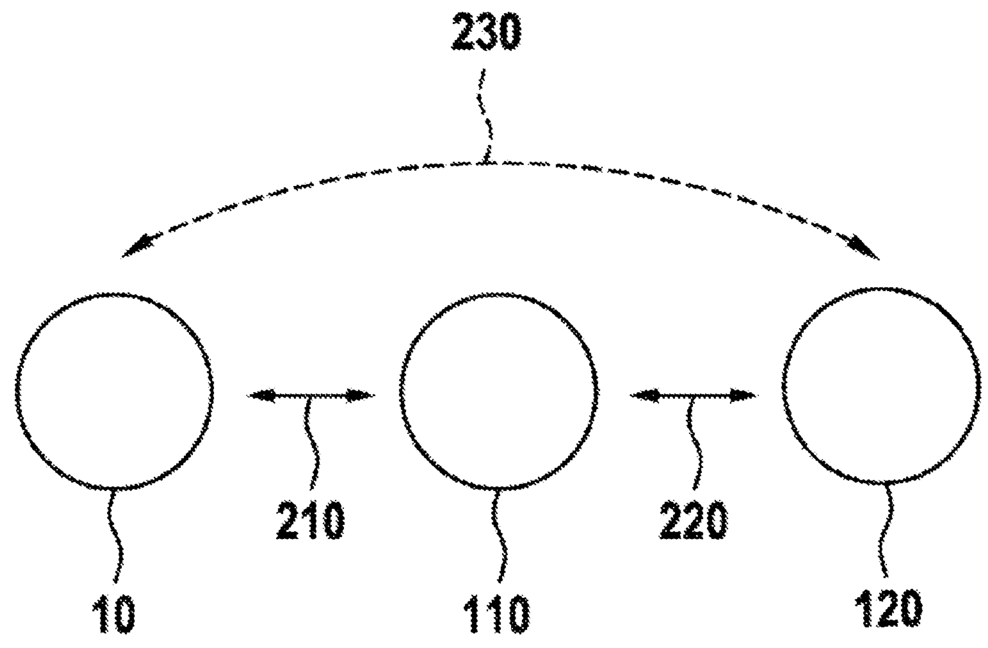

FIG. 2 schematically shows the communication paths 210, 220, 230 between a cardiac support system 10, the first extracorporeal control device 110 and the second extracorporeal control device 120. The first control device 110 is configured to communicate with the cardiac support system 10, either wirelessly, for example via Bluetooth®, or via a driveline. Information about states such as pump data, for example, is exchanged between the first control device 110 and the cardiac support system 10. The first control device 110 and the second control device 120 are furthermore configured to communicate wirelessly with one another. They are in particular configured to transmit changes in the settings and/or additional status information such as the charge states of the energy stores 160, 161 to one another and then adjust. The first control device 110 is preferably set up as a server and the second control device 120 as a client in a network configuration. The cardiac support system 10 can thus be controlled by the second extracorporeal control device 120 via the first extracorporeal control device 110. In a preferred embodiment, the cardiac support system 10 and the second control device 120 can furthermore be configured for wireless communication 230 with one another, which enables direct control of the cardiac support system 10 by the second control device 120. This also has the advantage that information about the cardiac support system 10 can be obtained directly by both control devices 110, 120, and both control devices 110, 120 can control the cardiac support system 10 directly. It is in particular possible for the user or patient to operate the cardiac support system 10 directly using only the second control device 120.

Figure 3:
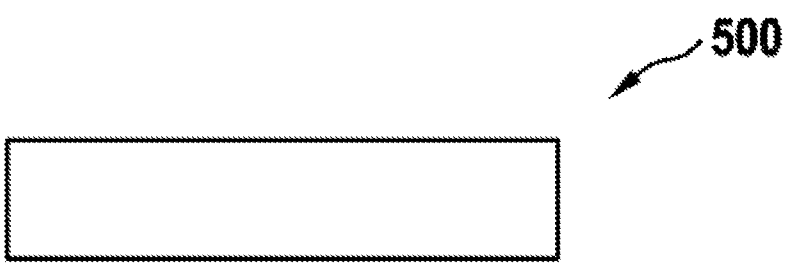

FIG. 3 shows a block diagram of a design example of the method 500 according to the invention, which can, for example, be carried out using a design example of the system 100 according to the invention as described above. According to the design example 500, the cardiac support system can be controlled via a first extracorporeal control device. The cardiac support system can also be controlled as described above via a second extracorporeal control device which is coupled wirelessly to the first control device or directly via a second extracorporeal control device which is coupled wirelessly to the cardiac support system. If the second control device is wirelessly connected to the first control device, the cardiac support system can be controlled by the second extracorporeal control device via the first extracorporeal control device.

The invention claimed is:

1. A system for controlling a cardiac support device, the system comprising:

a first energy source;

a first extracorporeal control device detachably connectable to the first energy source and comprising:

a first user input interface configured to receive user input including commands to change one or more settings of a pump of the cardiac support device;

a first coil configured to connect the first extracorporeal control device to the cardiac support device for communication or energy transfer;

a first communication interface configured to receive wireless instructions to control the pump of the cardiac support device and to transmit changes to one or more settings of the pump made at the first user input interface; and processing circuitry configured to cause transfer of energy from the first energy source to the cardiac support device via the first coil; and a second extracorporeal control device communicatively coupled to the first extracorporeal control device in a client-server configuration, detachably connectable to the first energy source and comprising:

a second user input interface configured to receive user input including commands to change the one or more settings of the pump of the cardiac support device;

a second communication interface configured to:

receive user input comprising a command to change the one or more settings of the pump of the cardiac support device;

wirelessly connect the second extracorporeal control device to the first extracorporeal control device, provide the command to control the one or more settings of the pump made at the second user input interface to the first extracorporeal control device, the first user input interface to control the pump of the cardiac support device based on the command, and processing circuitry configured to cause transfer of energy to the cardiac support device, from the first energy source or from a detachably connectable second energy source;

wherein during operation of the cardiac support device, the pump of the cardiac support device is controlled by the first extracorporeal control device when the command received via the first user input interface is provided to the cardiac support device and controlled by the second extracorporeal control device when the command received via the second user input interface is provided to the cardiac support device via the first extracorporeal control device.

2. The system of claim 1, wherein the second extracorporeal control device is configured to be a redundant device to the first extracorporeal control device.

3. The system of claim 1, wherein the first extracorporeal control device is configured as a server and the second extracorporeal control device is configured as a client in a network configuration.

4. The system of claim 1, wherein the first extracorporeal control device and the second extracorporeal control device are structurally identical.

5. The system of claim 1, wherein the first energy source is configured to be detachably connected to the first extracorporeal control device via a latch or click mechanism.

6. The system of claim 1, further comprising a second energy source configured to detachably connect to the second extracorporeal control device via a latch or click mechanism.

7. The system of claim 1, wherein:

the first extracorporeal control device is configured to receive a first input comprising a first change associated with one or more settings of the first extracorporeal control device and cause the second extracorporeal control device to make the first change associated with one or more settings of the second extracorporeal control device; and the second extracorporeal control device is configured to receive a second input comprising a second change associated with the one or more settings of the second extracorporeal control device and cause the first extracorporeal control device to make the second change to the one or more settings of the first extracorporeal control device.

8. The system of claim 1, wherein at least one of the first extracorporeal control device and the second extracorporeal control device comprises a display configured to receive input commands.

9. The system of claim 1, wherein at least one of the first extracorporeal control device and the second extracorporeal control device is configured to output an alarm signal when a distance between the first extracorporeal control device and the second extracorporeal control device exceeds a predetermined distance.

10. The system of claim 1, wherein at least one of the first extracorporeal control device and the second extracorporeal control device is configured to output an alarm signal if a signal strength or a signal quality between the first extracorporeal control device and the second extracorporeal control device is less than a predetermined threshold.

11. A cardiac support system comprising:

a first energy source;

a cardiac support device;

a first extracorporeal control device detachably connectable to the first energy source and comprising:

a first user input interface configured to receive user input including commands to change one or more settings of a pump of the cardiac support device;

a first coil configured to connect the first extracorporeal control device to the cardiac support device for communication or energy transfer;

a first communication interface configured to receive wireless instructions to control the pump of the cardiac support device and to transmit changes to one or more settings of the pump made at the first user input interface; and processing circuitry configured to cause transfer of energy from the first energy source to the cardiac support device via the first coil; and a second extracorporeal control device communicatively coupled to the first extracorporeal control device in a client-server configuration, detachably connectable to the first energy source and comprising:

a second user input interface configured to receive user input including commands to change the one or more settings of the cardiac support device;

a second communication interface configured to:

receive user input comprising a command to change the one or more settings of the pump of the cardiac support device;

wirelessly connect the second extracorporeal control device to the first extracorporeal control device, provide the command to control the one or more settings of the pump made at the second user input interface to the first extracorporeal control device, the first user input interface to control the pump of the cardiac support device based on the command, and processing circuitry configured to cause transfer of energy to the cardiac support device, from the first energy source or from a detachably connectable second energy source;

wherein during operation of the cardiac support device, the pump of the cardiac support device is controlled by the first extracorporeal device when the command received via the first user input interface is provided to the cardiac support device and controlled by the second extracorporeal control device when the command received via the second user input interface is provided to the cardiac support device via the first extracorporeal control device.

12. A method for controlling a cardiac support device, the method comprising:

establishing a first communication path between the cardiac support device and a first extracorporeal control device, the first extracorporeal control device configured to control the cardiac support device, receive information comprising pump data associated with the cardiac support device, receive, via a first user input interface, user input including commands to change one or more settings of a pump of the cardiac support device, and transmit the user input relating to the one or more settings of the pump made at the first user input interface of the first extracorporeal control device to the cardiac support device; and establishing a second communication path between a communication interface of the first extracorporeal control device and a communication interface of a second extracorporeal control device, the second extracorporeal control device configured for simultaneous use with the first extracorporeal control device and configured to:

receive, via a second user input interface, user input comprising a command to change the one or more settings of the pump of the cardiac device, provide the command to control the one or more settings of the pump made at the second extracorporeal control device to the first extracorporeal control device, control the cardiac support device via the first extracorporeal control device according to the command to control the one or more settings of the pump made at the second extracorporeal control device, and receive the changes made at the first extracorporeal control device the second communication path, and the first communication path, wherein the first extracorporeal control device and the second extracorporeal control device each comprise processing circuitry configured to cause transfer of energy from one or more detachably connectable energy sources to the cardiac support device via a coil, and wherein during operation of the cardiac support device, the cardiac support device is controllable by the user input to the first extracorporeal device via the first user input interface and by the user input to the second extracorporeal device via the second user input interface that is provided to the first extracorporeal device.

13. The method of claim 12, further comprising:

establishing a third communication path between the second extracorporeal control device and the cardiac support device, wherein the second extracorporeal control device is configured to control the cardiac support device via the third communication path.

14. The method of claim 12, wherein the first extracorporeal control device is configured as a server and the second extracorporeal control device is configured as a client in a network configuration.

15. The method of claim 12, wherein the first extracorporeal control device and the second extracorporeal control device are structurally identical.

16. The method of claim 12, further comprising detachably connecting a first energy source to the first extracorporeal control device.

17. The method of claim 12, further comprising detachably connecting a second energy source to the second extracorporeal control device.

18. The method of claim 12, further comprising:

receiving, via one of the first extracorporeal control device and the second extracorporeal control device, a first input comprising a first change associated with one or more settings of one of the first extracorporeal control device and the second extracorporeal control device;

causing another of the first extracorporeal control device and the second extracorporeal control device to make the first change associated with one or more settings.

19. The method of claim 12, wherein at least one of the first extracorporeal control device and the second extracorporeal control device comprises a display configured to receive input commands.

20. The method of claim 12, wherein at least one of the first extracorporeal control device and the second extracorporeal control device is configured to output an alarm signal when a distance between the first extracorporeal control device and the second extracorporeal control device exceeds a predetermined distance.

* * * * *